United States Patent

Kleinerman

[11] Patent Number: 5,820,265
[45] Date of Patent: Oct. 13, 1998

[54] OPTICAL SYSTEMS FOR SENSING TEMPERATURE AND THERMAL INFRARED RADIATION

[76] Inventor: Marcos Y. Kleinerman, 24 Jerome St., Southbridge, Mass. 01550

[21] Appl. No.: 645,595

[22] Filed: May 13, 1996

Related U.S. Application Data

[60] Division of Ser. No. 182,297, Jan. 14, 1994, Pat. No. 5,560,712, which is a continuation-in-part of Ser. No. 654,809, Feb. 13, 1991, Pat. No. 5,302,025, which is a division of Ser. No. 711,062, Mar. 12, 1985, Pat. No. 5,004,913, which is a continuation-in-part of Ser. No. 608,932, May 14, 1984, Pat. No. 4,708,494, which is a continuation of Ser. No. 405,732, Aug. 6, 1982, abandoned.

[51] Int. Cl.⁶ ............................ G01K 11/32; G01K 3/06; G02B 6/16
[52] U.S. Cl. .................... 374/137; 374/161; 250/227.14; 385/12; 385/123; 385/141
[58] Field of Search ................................... 374/161, 131, 374/120, 121, 124, 137; 250/227.14; 385/12, 141, 144, 123, 13

[56] References Cited

U.S. PATENT DOCUMENTS

| | | | |
|---|---|---|---|
| 3,456,211 | 7/1969 | Koester | 372/6 |
| 3,615,312 | 10/1971 | Landry et al. | 385/123 |
| 3,938,385 | 2/1976 | Horwath | 374/137 |
| 4,050,895 | 9/1977 | Hardy et al. | 385/12 |
| 4,070,091 | 1/1978 | Taylor et al. | 385/126 |
| 4,260,219 | 4/1981 | Greubel et al. | 385/141 |
| 4,295,739 | 10/1981 | Meltz et al. | 385/126 |
| 4,342,907 | 8/1982 | Macedo et al. | 374/131 |
| 4,372,648 | 2/1983 | Black | 385/144 |
| 4,437,772 | 3/1984 | Samulski | 374/131 |
| 4,592,664 | 6/1986 | Bijlenga et al. | 374/131 |
| 4,600,310 | 7/1986 | Cramp et al. | 385/123 |
| 4,673,299 | 6/1987 | Dakin | 374/161 |
| 4,708,494 | 11/1987 | Kleinerman | 374/161 |
| 4,767,219 | 8/1988 | Bibby | 374/131 |
| 4,823,166 | 4/1989 | Hartog et al. | 374/131 |
| 4,834,496 | 5/1989 | Blyler, Jr. et al. | 385/127 |
| 5,004,913 | 4/1991 | Kleinerman | 374/131 |
| 5,052,820 | 10/1991 | McGinniss et al. | 374/131 |
| 5,096,277 | 3/1992 | Kleinerman | 385/12 |
| 5,302,025 | 4/1994 | Kleinerman | 374/131 |
| 5,363,463 | 11/1994 | Kleinerman | 385/12 |
| 5,499,313 | 3/1996 | Kleinerman | 385/12 |

*Primary Examiner*—Diego F. F. Gutierrez

[57] ABSTRACT

Optical temperature sensors use a temperature-dependent relative distribution of the intensity of interrogating light of wavelengths $\lambda_1$ between two light-guiding regions of a light-guiding probe. The relative distribution can be determined by a plurality of means including the spatial separation of the lights carried by the two light-guiding regions, and/or the conversion of one of the lights into light of wavelengths $\lambda_2$ different and easily separable from light of wavelength $\lambda_1$. The sensors can be adapted to measure infrared radiation by measuring its heating effect on the sensing probes and to convert a thermal infrared image into a visible image.

12 Claims, 8 Drawing Sheets

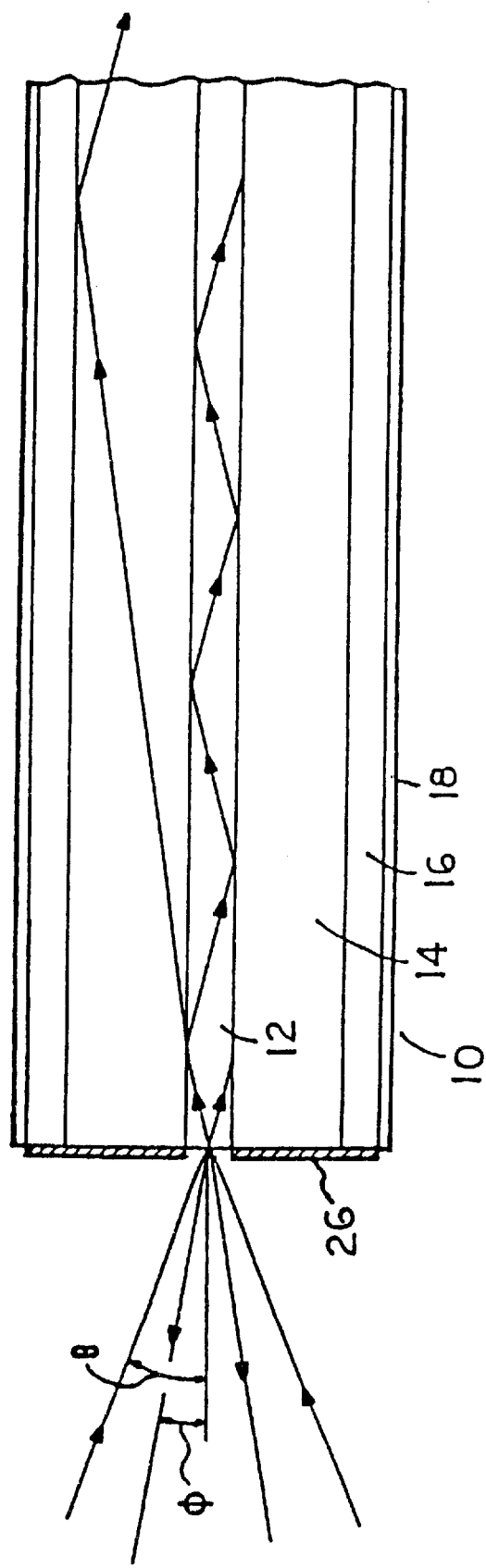

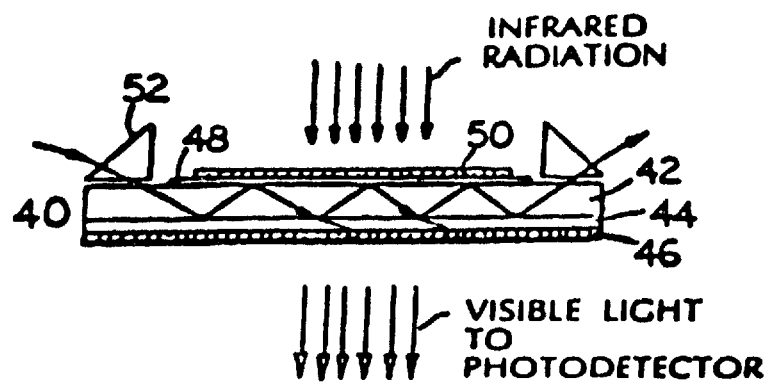
FIG. 6
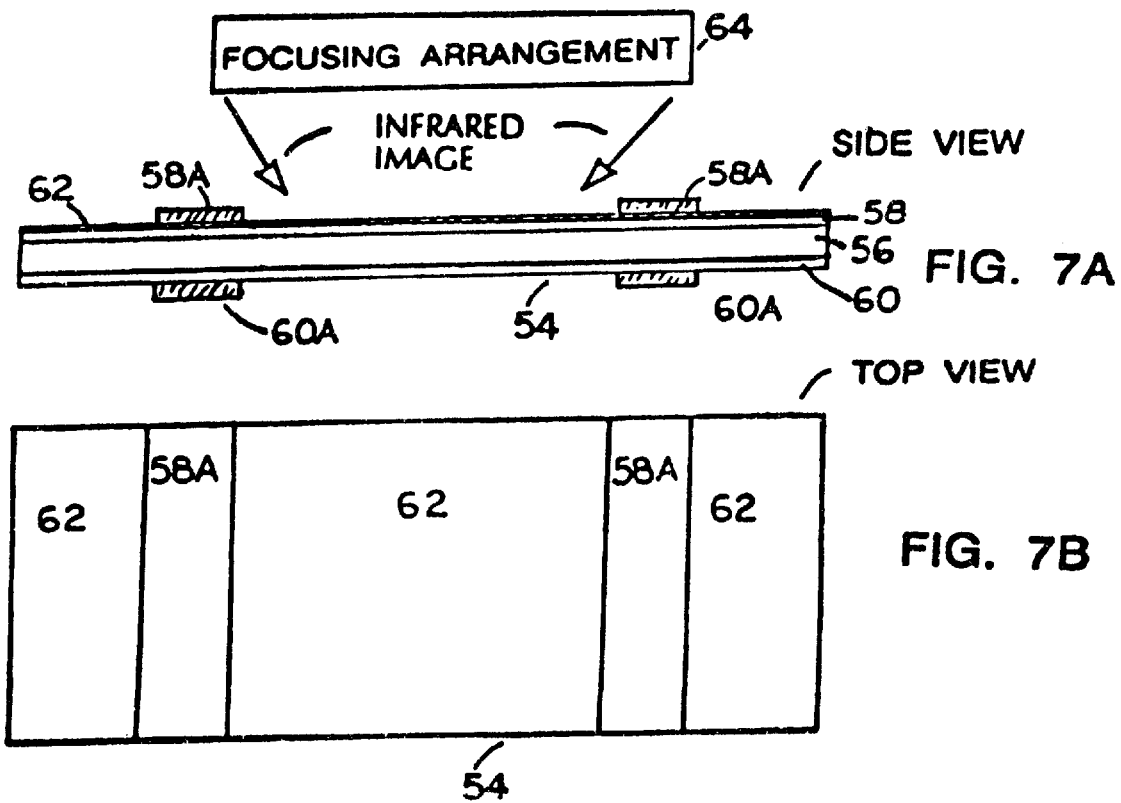
FIG. 7A
FIG. 7B

OPTICAL SYSTEMS FOR SENSING TEMPERATURE AND THERMAL INFRARED RADIATION

CROSS-REFERENCE TO RELATED APPLICATIONS

This is a division of application Ser. No. 08/182,297 filed Jan. 14, 1994, now U.S. Pat. No. 5,560,712, which in turn is a continuation-in-part (CIP) of application Ser. No. 07/654,809 filed Feb. 13, 1991, now U.S. Pat. No. 5,302,025, which in turn is a division of application Ser. No. 711,062 filed Mar. 12, 1985, now U.S. Pat. No. 5,004,913, which in turn is a CIP of application Ser. No. 608,932 filed May 14, 1984, now U.S. Pat. No. 4,708,494, which in turn is a continuation of application Ser. No. 405,732 filed Aug. 6, 1982, now abandoned. The subject matter of sections 3.0 to 3.2 is covered in application Ser. No. 08/305,252, now U.S. Pat. No. 5,499,313 and was also covered in application Ser. No. 815,741 filed Jan. 2, 1992, now U.S. Pat. No. 5,363,463, the teachings of which are incorporated herein by reference.

BACKGROUND OF THE INVENTION AND DESCRIPTION OF THE PRIOR ART

The present invention relates to improved methods and devices for sensing temperature changes and changes in the magnitude of any other physical field which can produce a temperature change, including but not limited to infrared radiation, especially radiation of wavelengths longer than about 2.0 micrometers ($\mu$m), referred to hereinafter as "thermal infrared radiation".

Prior art methods and devices for measuring temperature include the use of probes made of materials having temperature-dependent photo-luminescence properties. One of the earliest systems was described in U.S. Pat. No. 2,551,650 of Urbach, and used a photo-luminescent material the luminescence intensity of which was quenched appreciably with an increase of temperature. Luminescence quenching is usually associated with a decrease of the luminescence decay time of the material following excitation of its luminescence by pulsed or oscillatory light of wavelengths within an electronic absorption band characteristic of the material. Since the measurement of a luminescence decay time is usually more accurate and reliable than the measurement of a luminescence intensity (especially in the absence of intensity referencing), some recent temperature measurement techniques using photo-luminescent probes have used the temperature-dependent luminescence decay time as temperature indicator. These decay time techniques were used in a plurality of fiber optic temperature measuring techniques, including among others those described in U.S. Pat. Nos. 4,223,226 and 4,245,507 and in a publication by J. S. McCormack (*Electronics Letters* 17, 630 [1981]). These prior art-techniques have, however, a serious disadvantage: As temperature increases, the signal strength and, hence, the measurement accuracy, decrease. This limits severely the temperature range of operation of probes which have a temperature coefficient of decay time of the order of one percent or better, so a wide temperature range can be achieved only with probes having a significantly lower temperature coefficient of decay time and, hence, a significantly lower sensitivity and accuracy. Other prior art techniques for the optical measurement of temperature include the measurement of the temperature-dependent changes of the spectral distribution of the luminescence of some phosphors, as described in U.S. Pat. Nos. 3,639,765 and 4,061,578, among others.

None of the above techniques are suitable for measuring small temperature changes of the order of $10^{-2}$ kelvins (K) or smaller, as such measurements would require the capability of measuring minute changes of light intensity with an accuracy better than one part in 10,000.

The sensing of infrared radiation is most commonly carried out by electrical sensors. Two main kinds of sensors are: (a) quantum detectors, and (b) thermal detectors. The quantum detectors operate by converting a number N of infrared photons incident on the active surface of the detector into a number qN of free charges (electrons or "holes"), where q is the quantum efficiency of the detector. By contrast, the thermal detectors are essentially electrical temperature sensors which respond to the temperature rise of the active surface of the detector caused by the absorption of the infrared radiation.

There are also infrared sensors which are entirely optical. They are far less common than the electrical sensors, and are used in specialized applications. They also comprise quantum detectors and thermal detectors. The quantum detectors typically require a two-step excitation process, wherein a relatively high energy optical "pump" beam excites the molecules or atoms of the detector to an intermediate excited level. Then the infrared photons to be detected further excite these molecules or atoms to a higher energy level, from which they decay to the ground level by emission of visible radiation. The intensity of the emitted visible radiation is then an indicator of the intensity of the infrared radiation.

The optical thermal detectors include, for example, the rare earth-doped luminescent materials subject of U.S. Pat. Nos. 3,639,765 and 4,061,578. These infrared detectors of low thermal mass which are activated by ultraviolet or short wavelength visible radiation and emit luminescence light, the spectral distribution of which is a sensitive function of temperature. The infrared radiation is detected by the temperature increase caused by the absorbed infrared radiation, and its modulation of the sensor luminescence.

OBJECTS OF THE INVENTION

It is an object of this invention to provide methods and devices for sensing temperature, based on new ways of using the temperature-dependence of the transmission of light in certain light guides.

It is another object of this invention to provide a new technique whereby said temperature dependence of the index of refraction of the component of a light guide can be used for measuring minute temperature changes, suitable for measuring changes of the order of $10^{-3}$ kelvins or smaller.

Still another object of the present invention is to use the temperature-sensing systems disclosed herein for sensing infrared radiation through the temperature changes generated by the absorption of this radiation, and for converting an infrared image into a visible image.

Other objects of the present invention will in part be apparent from the following discussion and will in part appear hereinafter.

SUMMARY OF THE INVENTION

The objects of this invention are accomplished by the use of film light guides including a first light-guiding region comprised of a first material having an index of refraction $n_1$ into which is injected an interrogating light of pre-selected visible or near infrared wavelengths. This light-guiding region is in contact with a second region comprised of a second material having an index of refraction $n_2$ lower than $n_1$. A temperature change causes changes in the transmission properties of said interrogating light.

In one embodiment the indices of refraction $n_1$ and $n_2$ have substantially different temperature coefficients in such a manner that an increase in temperature causes a temperature-dependent fraction of the intensity of the interrogating light propagating along the light guide to be ejected from it. In another embodiment the first light guiding region has a photoluminescent material dissolved therein which absorbs a temperature-dependent fraction of the intensity of the interrogating light, causing the emission of luminescence light having an intensity which varies in a known manner with temperature.

DEFINITIONS

Within the context of this application, I am using the following definitions:

Light: optical radiation, whether or not visible to the human eye.

Occupancy number of an energy level: the fraction of the total number of molecules of a probe material occupying said energy level.

Vibronic material: any luminescent material whose molecular electronic ground energy level comprises a plurality of vibrational sublevels with energies higher that of the lowest occupied level of the material, said vibrational sublevels being so distributed as to cover an essentially continuous wide band of energies.

Vibronic level: a vibrational sublevel of the electronic ground level of a vibronic material, having an occupancy number which increases with increasing temperature.

Luminescence: Light emitted by a material upon absorption of light or other radiation of sufficient quantum energy. The term includes both fluorescence and phosphorescence.

Photoluminescence: Luminescence generated by the absorption of light.

Luminescence centers: atoms or molecules (including ions) of a luminescent material which absorb excitation light and emit luminescence light.

Luminescence quantum efficiency $\phi$ (also referred to as luminescence efficiency): the ratio of the number of luminescence photons emitted by a luminescent material to the number of photons of the excitation light absorbed by the material.

Luminescence decay time $\tau$: the time after the cessation of the excitation radiation in which the intensity of the luminescence decays from $I_o$ to $I_o/e$, where e is equal to 2.71828 and $I_o$ is the luminescence intensity at any reference time chosen as "zero" time.

Luminescence time rate of decay: the inverse of luminescence decay time.

Physical variable: any physical property whose magnitude can change. Examples: temperature, pressure, flow rate, position, liquid level, and the like.

Physical parameter: physical variable.

Interrogating light: illuminating light injected into an optical probe for the physical variable.

Excitation light: illuminating light which can generate luminescence in a luminescent material.

Light beam: light being propagated through an optical system, including optical fibers, regardless of degree of divergence.

Thermal infrared radiation: infrared radiation having wavelengths longer than 2.0 micrometers.

BRIEF DESCRIPTION OF THE DRAWINGS

FIG. 3 illustrates an optical fiber probe for measuring distributed temperatures according to the invention.

FIG. 6 illustrates an arrangement for sensing infrared radiation according to the invention.

FIG. 7 shows an arrangement for converting a thermal infrared image into a visible image according to the invention.

DETAILED DESCRIPTION OF THE INVENTION

1.0 New Fiber Optic Sensors Based on Core/Cladding Light Redistribution.

Figure 1A:
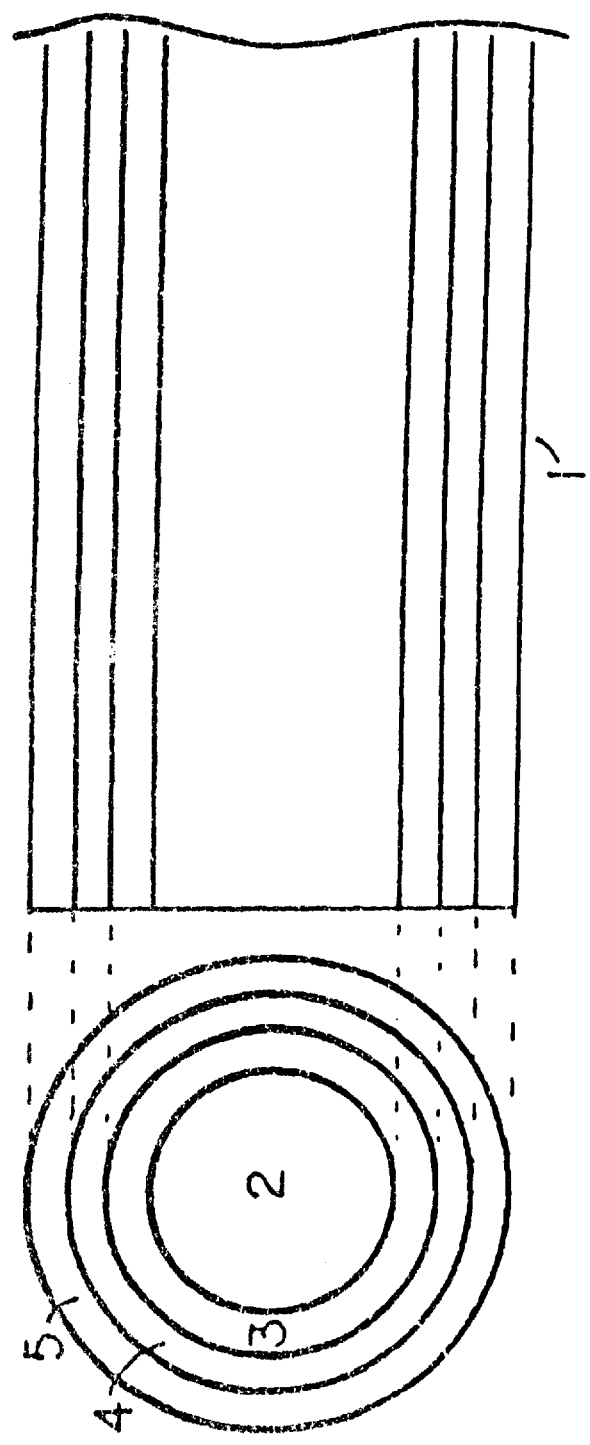
FIG. 1 illustrates an optical fiber including a luminescent cladding, suitable for sensing changes in the magnitude of a physical parameter according to this invention.
Figure 1B:
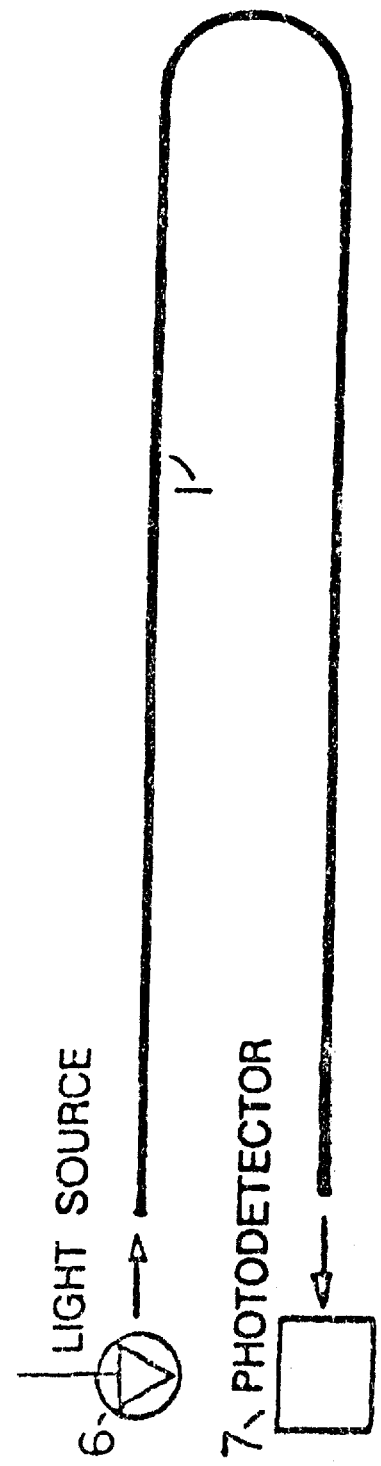

FIG. 1 illustrates an embodiment of a new system, based on the present invention, for measuring the ratio of the intensity of the core modes to that of the cladding modes in an optical fiber. The system uses as a sensing probe an optical fiber 1 having a clear core 2 with an index of refraction $n_1$, a clear cladding 3 having an index of refraction $n_2$ lower than $n_1$, a second cladding 4 with an index of refraction $n_3$ not lower than $n_2$ and having dissolved therein a photoluminescent solute which will absorb at least part of the fraction of the intensity of the interrogating light beam injected into the core which is coupled to the cladding under the action of a physical variable, and an outer cladding 5 with an index of refraction $n_4$ lower than $n_2$. The system works as follows:

A light source 6 launches (injects) an interrogating light beam of wavelengths $\lambda_1$ into the fiber core 2. The variable physical field (variable) F being sensed causes a change in the magnitude of the fraction of the intensity of the interrogating light injected into the core 2 which is deflected into cladding 4 through cladding 3. This causes a change in the intensity of the luminescence light of wavelengths $\lambda_2$ generated at the cladding 4. Both the undeflected interrogating light and a fraction of the intensity of the luminescence light are directed to the photodetection station 7 where the two lights are measured by techniques known in the art. The relative intensities of these two lights are an indicator of the magnitude of the physical variable acting on the fiber.

Cladding 4 can be a glass doped with an inorganic photoluminescent ionic species or an organic polymer doped with a fluorescent dye. Examples of inorganic photoluminescent specie are trivalent chromium and trivalent rare earth ions selected from the group comprising neodymium, ytterbium, erbium, samarium, holmium, thulium and europium. There is a very large number of fluorescent dyes which can be dissolved in the organic polymer constituting cladding 4. Dyes which can be excited with available light-emitting diodes (LEDs) or laser diodes (LDs) include, for example, those of the bis-benzanthrone family of dyes, for example Vat Green 1.

1.1 A Simple Fiber Optic Thermometer.

Figure 2A:
FIG. 2 illustrates an optical fiber having two polymeric claddings, used as a temperature probe according to this invention.
Figure 2B:
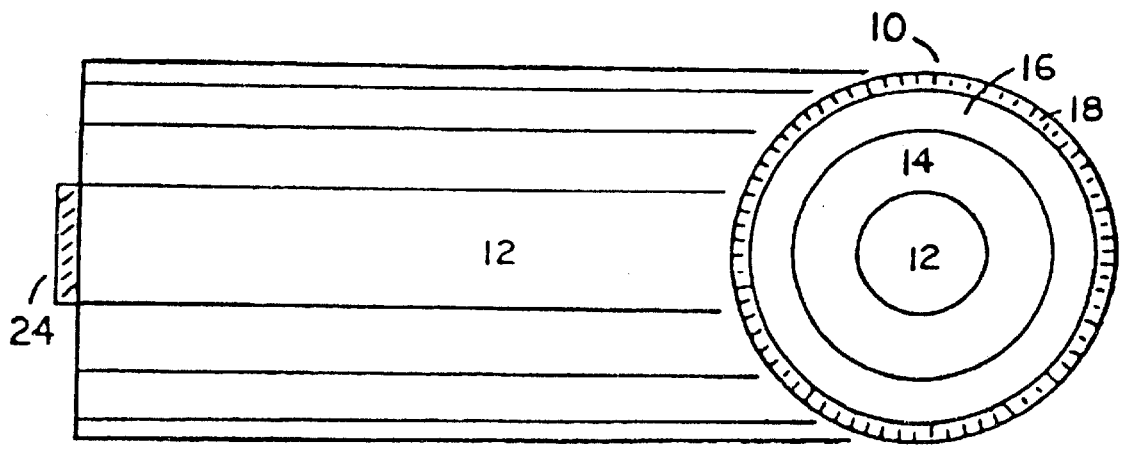

An embodiment of a thermometer according to this invention is illustrated in FIG. 2. It uses as a probe an optical fiber 10 including a glass core 12 having an index of refraction $n_1$, and two concentric plastic claddings. The first cladding 14 immediately surrounding the core has an index of refraction $n_2$ lower than $n_1$. The second cladding 16 around the first cladding has an index of refraction $n_3$ lower than $n_2$. The temperature coefficients of $n_2$ and $n_3$ are approximately equal, and substantially greater than the temperature coefficient of $n_1$. Cladding 16 is covered by a black or otherwise light-absorbing coating 18. The numerical apertures $(NA)_1$ and $(NA)_2$ of core 12 and cladding 14, respectively, are given by the relations $$(NA)_1 = (n_1^2 - n_2^2)^{1/2} \quad (1)$$

and $$(NA)_2 = (n_2^2 - n_3^2)^{1/2} \quad (2)$$

Since the value of $n_2$ decreases with increasing temperature at a much higher rate than the change of the value of $n_1$, the value of $(NA)_1$ increases substantially with increasing temperature. In most inorganic glasses, including silica, the value of $n_1$ changes so little with increasing temperature compared to index changes of plastics, that it may be regarded as essentially constant for the purposes of this description. Thus, the value of $(NA)_2$ is regarded as essentially invariant.

In operation, the fiber is bent at its sensing point, to fill the numerical aperture of both core 12 and cladding 14 when interrogating light is launched into the fiber by the light source 20. The distribution of the intensity of the interrogating light between the core 12 and the cladding 14 will be determined uniquely by the fiber temperature at the bend. Since $(NA)_2$ is substantially independent of temperature, the total light intensity arriving at the fiber distal end will not vary significantly with temperature, but the fraction of this intensity propagating along the cladding at the fiber distal end will be a unique function of the temperature difference between the fiber distal end and its sensing point. Thus, if the temperature of the fiber distal end is controlled or just known, the probe temperature can be easily determined by measuring the intensity of the cladding light by photodetector 22 located at the fiber distal end. The core light is filtered out by miniature optical filter 24.

1.2 A Distributed Temperature Sensor Using a Single Optical Fiber Probe.

If the optical fiber 10 of FIG. 2 is made sufficiently long it can be used to measure temperature at a plurality of points distributed along its length, by using optical time domain reflectometry (OTDR) techniques. This is explained with reference to FIG. 3. An opaque coating 26 (for example an aluminum film) is applied to the face of the two claddings at the launch end of the fiber, so that the interrogating light can be launched only through core 12. The interrogating light is launched as a recurrent train of short pulses with a duration of the order of a few nanoseconds (ns) or shorter, depending on the spatial resolution desired (approximately 10 ns per fiber-meter), over an acceptance angle θ for meridional rays necessary to fill the numerical aperture $(NA)_2$. In other words, the interrogating light fills both light-guiding regions 12 and 14. The value of $n_2$ decreases in a known manner with an increase in temperature at a much higher rate than the decrease in the value of $n_1$, and the intensity distribution of the interrogating light pulses between regions 12 and 14 will be determined by the relative magnitudes of $(NA)_1^2$ and $(NA)_2^2$.

Now, the intensity of the light pulses Rayleigh-backscattered from core 10 at any resolvable segment of the fiber, corrected for the intrinsic light attenuation of the fiber per unit length, will be a known function of the temperature of that segment.

In contrast to prior art methods of temperature measurement based on a temperature-dependent index of refraction, crosstalk between different sensing points is minimized by virtue of the fact that light rays deflected out of core 12 by a temperature change are not 'thrown away' as in the prior art, but are captured and returned to the region comprising core 12 and first cladding 14, thus restoring a temperature-dependent light distribution at every resolvable segment of the fiber.

Since the cladding faces of the fiber at the launch end are aluminized (or otherwise made opaque), and the diameter of cladding 14 can be made much larger than that of core 12, the intensity of the Rayleigh-backscattered light collected at the core launch end from any resolvable segment of the fiber will be proportional to the intensity of the interrogating light propagating within the core along that segment, determined by the magnitude of $(NA)_1$ and, hence, by the temperature-dependent value of $n_2$. Any contribution from cladding 14 to the collected Rayleigh-backscattered light can be further minimized by using a small collection angle φ consistent with the signal intensity needed.

The sensitivity and performance of the distributed temperature sensor depends on the materials used for the plastic cladding 14. For example, if the values of $(NA)_1$ and $n_2$ are about 0.15 and 1.450, respectively, at the ambient temperature of 300K, and the temperature coefficient of $n_2$ is about $2 \times 10^{-4}$ per kelvin at this temperature, then a temperature change of 1 kelvin will produce a change in the intensity of the light Rayleigh-backscattered from core 12 of approximately 2.5 percent, a relatively large change compared to prior art fiber optic temperature sensing systems.

In a variation of the above technique, the second cladding 16 has dissolved therein a fluorescent dye at a concentration small enough not to alter significantly the temperature-dependent distribution of the interrogating light modes between the core 12 and the first cladding 14, but sufficient to generate fluorescence light pulses at the evanescent region of an intensity comparable to that of the Rayleigh-backscattered pulses from cladding 14. The intensity of the fluorescence light pulses is then indicative of the intensity of the modes of the interrogating light propagating along cladding 14. This variation has the advantage that one can measure simultaneously both the intensity of the core modes and that of the cladding modes, by Rayleigh backscattering and by fluorescence, respectively. An example of a suitable device for these measurements is described in the following paragraph, with the aid of FIG. 4.

Figure 4:
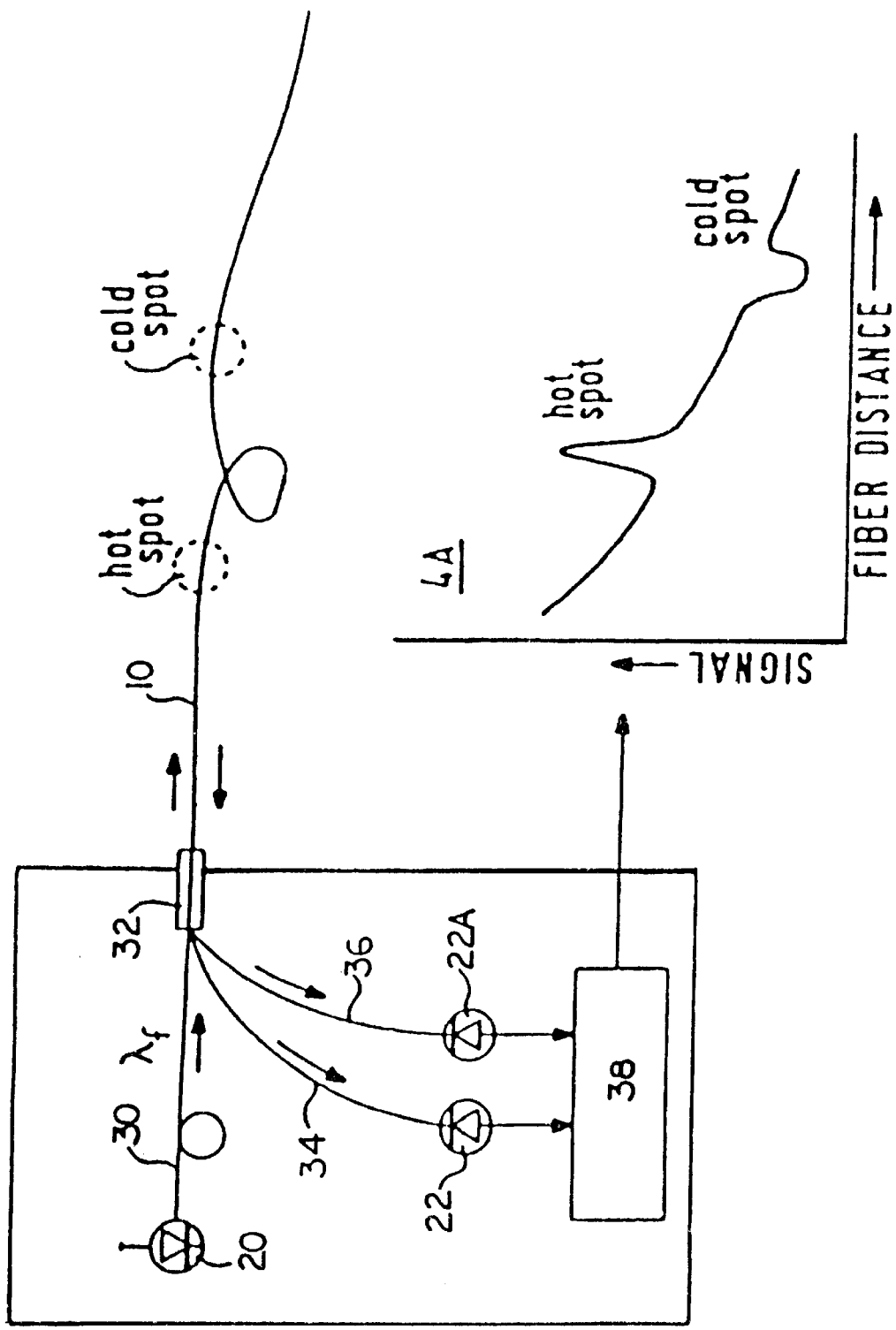
FIG. 4 illustrates a device for measuring distributed temperatures according to the invention.

Referring to FIG. 4, the light source 20 is driven to generate interrogating light pulses of a duration of the order of 10 ns and wavelengths $\lambda_1$. These light pulses are injected into the fiber segment 30 and, through the optical fiber coupler 32, into the core of the temperature-sensing fiber. At any point along the fiber, each interrogating light pulse generates a fluorescence light pulse of an intensity determined by the fiber temperature at that point, and a reference light pulse which is the Rayleigh backscatter of the interrogating light pulse. The intensities of these two pulses captured within the fiber are back-transmitted by the optical fiber to the coupler 32 and, via optical fiber segments 34 and 36, to photodetectors 22 and 22A, respectively. The time of arrival of these two pulses at the photodetectors, relative to the time of injection of the interrogating light pulses into the fiber 10, identifies the location of the temperature sensing point. The relative intensities of these two back-transmitted pulses, processed by the microprocessor 38, are an indicator of the fiber temperature at the sensing point.

1.3 A Differential Fiber Optic Thermometer

Figure 5:
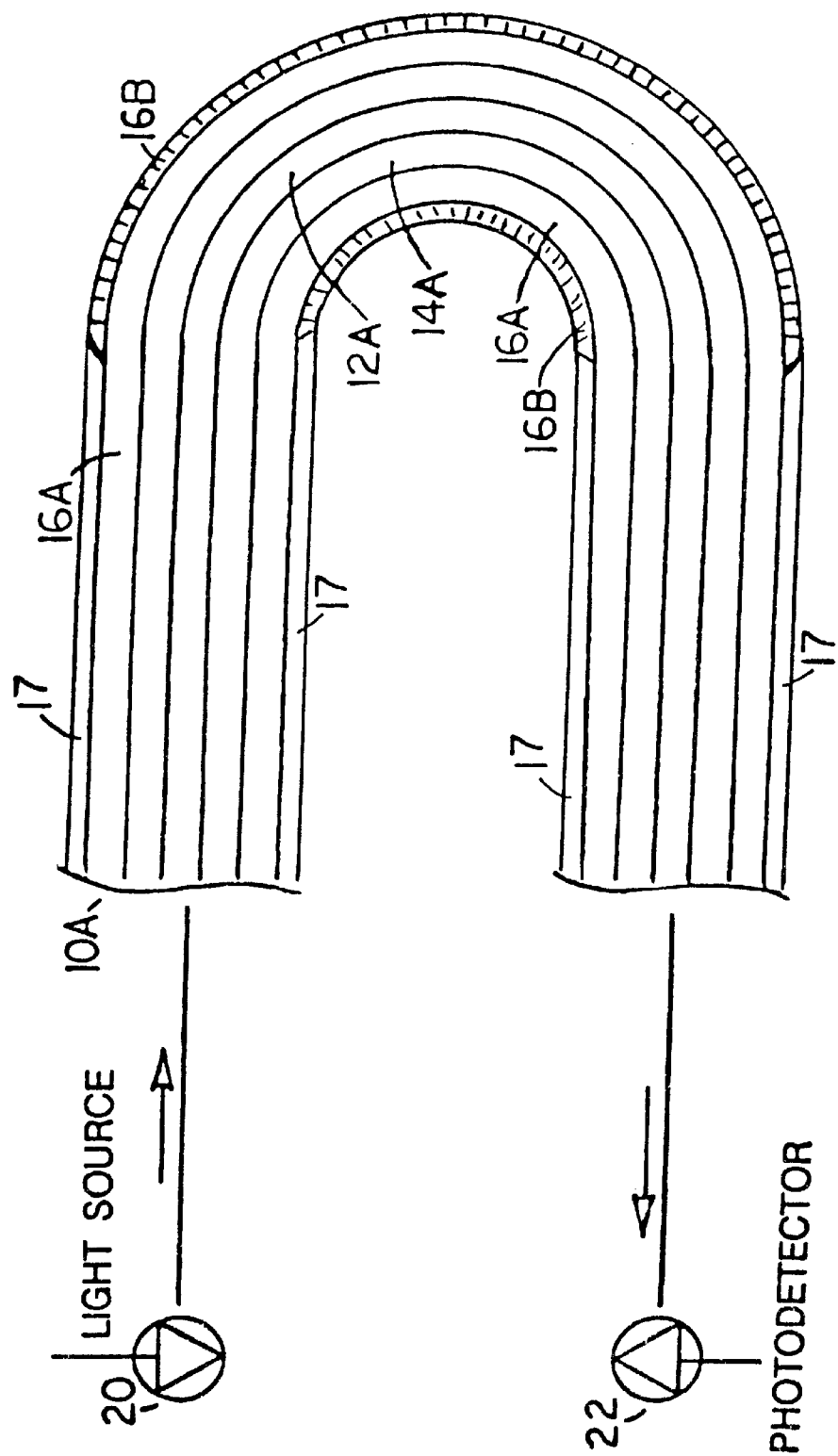
FIG. 5 shows a differential fiber optic thermometer according to this invention.

One preferred embodiment of the differential fiber optic thermometer is described with reference to FIG. 5. The probe is a multimode optical fiber 10A having a glass core 12A with an index of refraction $n_1$, and a clear elastomeric plastic cladding 14A with a thickness not greater than about 5 micrometers and an index of refraction $n_2$ lower than $n_1$ and which decreases with increasing temperature at a much higher rate than any change of the value of $n_1$. Around this cladding there is a second cladding 16A having a fluorescent dye dissolved therein and an index of refraction $n_3$ not lower than $n_2$. A short segment of this fiber exposed to the temperature to be measured has a black coating 16B on cladding 16A, to 'strip' the fluorescence cladding modes. Outside this segment, the fluorescent cladding 16A is covered with a transparent outer cladding 17 having an index of refraction $n_4$ lower than $n_2$. Within the segment of the fiber exposed to the temperature to be measured there is a bend designed to make the interrogating light launched by light source 20 fill the numerical aperture $(NA)_1$ of the fiber core. Because of the bend on the fiber, a substantial fraction of the intensity of the interrogating light launched into the fiber core is deflected to the fluorescent cladding, where it generates fluorescence light with an intensity proportional to the intensity of the deflected fraction. The black coating 16B 'strips' (removes) this fluorescence light from the fiber. Now, if the temperature of the exposed segment increases to $T_1$ relative to the fiber temperature $T_0$ just outside the segment in the direction of propagation of the interrogating light, the fraction of the intensity of the interrogating light deflected into the fluorescent cladding within said segment decreases as the numerical aperture of the fiber increases from $(NA)_{10}$ to $(NA)_{11}$. Thus, the intensity of the interrogating light propagating along the core 12A increases from $I_0$ to $(I_0+\Delta I)$. But as the interrogating light reaches the region of temperature $T_0$, the intensity increase $\Delta I$ is lost to the fluorescent cladding as the numerical aperture of the fiber core decreases to $(NA)_{10}$ from $(NA)_{11}$, there generating a fluorescence light with an intensity proportional to $\Delta I$.

This device is particularly suitable for monitoring exothermic chemical reactions, and as such can be used in enzymatic biochemical analysis.

It should be apparent to a person having at least average competence in the art that an optical fiber probe having a fluorescent cladding around a clear core can be used for sensing other physical parameters besides temperature. Any physical change which can cause the deflection of interrogating light from the core to a luminescent cladding, or affect the extent of said deflection, is measurable with such probe.

2.0 The Sensing of Thermal Infrared Radiation.

An embodiment of a device for sensing infrared radiation is described with reference to FIG. 6 (similar to FIG. 4 in the parent application Ser. No. 711,062, now U.S. Pat. No. 5,004,913) which illustrates one of the preferred embodiments of the invention. A thin film probe 40 comprises a light-guiding layer 42 preferably less than 10 micrometers thick, made of a material having an index of refraction $n_1$ with a relatively large negative temperature coefficient of the order of $10^{-4}$ per kelvin or greater, is in optical and mechanical contact with a transparent second layer 44 having an index of refraction $n_2$ lower than $n_1$, the temperature coefficient of $n_2$ being lower than that of $n_1$. A white light-scattering coating 46 is applied to the outside of layer 44. On its other surface layer 42 is in contact with a thin transparent layer 48 having an index of refraction $n_3$ lower than $n_2$, and having in turn a thin infrared absorbing coating 50 applied on it. A visible or near infrared light beam of wavelengths $\lambda_1$ is coupled to light-guiding layer 42 by means of prism 52, in such a manner as to couple into layer 42 all the light modes which the light-guiding layer can support. The beam propagates along the layer 42 by total internal reflection from layers 44 and 48, and with a number of angular modes which is a positive function of the magnitude of the numerical aperture $(NA)_p$ of the film probe, given by the relation $(NA)_p=(n_1^2-n_2^2)^{1/2}$. When infrared radiation is absorbed by coating 50 at any point along the film probe, the probe temperature increases at that point, and the magnitude of $(NA)_p$ decreases. This causes a fraction of the intensity of the visible or near infrared light propagating along layer 42 at that point to be deflected out of this layer. The deflected light is directed to a photodetector, generating an electrical signal therein, the magnitude of which is an indicator of the intensity of the infrared light incident on and absorbed by the light guide.

In an alternate embodiment, the light-scattering coating 46 may be replaced by a fluorescent coating which absorbs the light deflected from the film and converts it into luminescence light including wavelengths $\lambda_2$.

2.1 An Infrared Image Converter

The infrared image of a warm or hot object is essentially the spatial temperature distribution of that object. Therefore, the physical principles described in the preceding paragraphs can be applied to convert infrared images into visible images. One obvious way is to use scanning mirrors for sequentially focusing each resolvable element of the infrared image into the infrared sensing light guide used as a point detector. A more powerful technique uses a two-dimensional infrared sensing light guide in an arrangement described as follows, with reference to FIG. 7:

Referring to FIG. 7, the probe 54 is a two-dimensional film comprising a layer 56 having an index of refraction $n_1$, 'sandwiched' between layers 58 and 60. Light-guiding layer 56 differs from light guiding layer 42 of FIG. 6, and layers 58 and 60 differ respectively from layers 44 and 48 of the same figure, only in that they have a greater area, suitable for focusing a thermal image into the film probe. Their indices of refraction and the temperature dependence of these indices are the same. Layers 58 and 60 are painted black outside the area into which the infrared image is focused. Layer 58 is coated with the light-scattering coating 62. In operation, light of wavelengths $\lambda_1$ is injected into layer 56 uniformly from one or, preferably, two or more square sides. The injected light has an angular distribution such as to overfill its numerical aperture $(NA)_{56}$ defined by the relation $$(NA)_{56}=(n_1^2-n_2^2)^{1/2}.$$

The light rays having angles smaller than the critical angle $\theta_c$ for total internal reflection (referenced to the normal to the plane of the film) enter layer 58 and are 'stripped' by the black stripes 58A and 60A on layers 58 and 60. The light rays having an angle greater than $\theta_c$ will propagate inside light guide 56 by total internal reflection at the boundaries between layer (light guide) 56 and layers 58 and 60. The thermal infrared image to be processed is focused into the film probe 54 by means of the focusing arrangement 64, which can be a lens system or a focusing mirror arrangement well known in the art. The focused infrared image increases the temperature at all points in the film, generating a two-dimensional temperature distribution, the temperature increase at each point increasing in a known manner with the intensity of the infrared radiation incident at that point. At each point where the incident infrared radiation raises the temperature of the film, a fraction of the intensity of the light of wavelengths $\lambda_1$ propagating within light guide 56 will be deflected out of the light guide through layer 58 into coating 62, from where it is emitted as light of wavelengths $\lambda_1$ and an intensity increasing in a known manner with the intensity of the infrared radiation incident at that point. The light of wavelengths $\lambda_1$ emitted from all points heated by the focused infrared image is then an image corresponding to the infrared image focused on the two-dimensional film. This image is then converted into a TV-type display by means of a TV camera.

In a variation of the above arrangement, coating 62 is replaced by a plastic film having a fluorescent dye dissolved therein. The dye is chosen so that it absorbs at least part of the intensity of the light of wavelengths $\lambda_1$ deflected from the light guide 56 and converts it into fluorescence light of wavelengths $\lambda_2$ different from $\lambda_1$ emitted from the film probe. The thermal infrared image is thus converted into a fluorescence light image, which can be converted into a TV display by a standard TV camera.

3.0 Temperature Sensing Based on the Direct Measurement of Thermally Activated Light Absorption and Emission Processes.

The techniques described in this section make use of thermally activated light absorption by optical probes and emission of light at wavelengths different from the wavelength or wavelengths of the interrogating light. A preferred embodiment uses photoluminescent probes, but does not require any photoluminescence property which varies with temperature over the temperature range being measured, and can be implemented with probes made of virtually any solid or liquid photo-luminescent material. These techniques were disclosed extensively in the preceding application Ser. No. 608,932 filed May 14, 1984, now U.S. Pat. No. 4,708,494. A thorough discussion is found in the specification of said patent, from column 6, line 50 to column 11, line 50. Device embodiments are described in column 15, lines 11–61 and FIGS. 1 and 5. A preferred embodiment uses probes operated according to the principles described and illustrated with reference to FIG. 8. The analysis that follows is deliberately oversimplified to emphasize the aspects most relevant to the invention. The quantitative relationships may not be followed rigorously in all practical systems.

Figure 8:
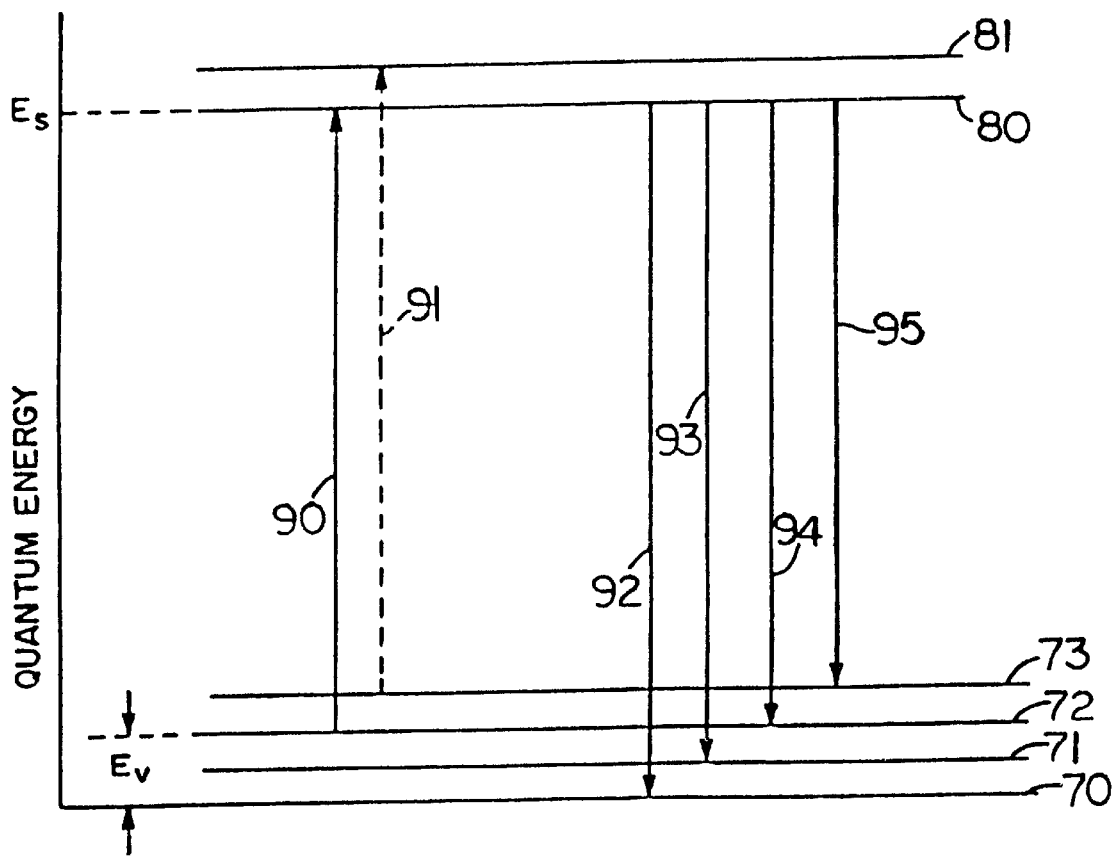
FIG. 8 is a simplified molecular energy diagram illustrating a temperature-dependent optical absorption process and luminescence conversion of the absorbed light in most luminescent materials.

FIG. 8 shows an electronic energy level diagram which at least qualitatively describes, at the molecular level, most photoluminescent materials. The photoluminescent material includes, at the atomic or molecular level, luminescence centers having a ground electronic level comprising vibrational sublevels 70, 71, 72, 73 and other sublevels which, for the sake of simplicity, are not shown. These materials are referred herein as "vibronic" materials. The lowest excited electronic energy comprises vibrational sublevels 80, 81, and other vibrational sublevels not shown. The vertical arrowed line 90 represents an optical electronic transition produced by the absorbed excitation light from level 72 to vibrational sublevel 80, which have fixed energy levels $E_v$ and $E_s$, respectively, relative to level 40. The length of line 90 corresponds to the photon energy of the optical transition and, hence, to the specific wavelength $\lambda_v$ of the excitation light. This wavelength obeys the relation $$\lambda_v = hc/(E_s - E_v)$$

where h is Planck's constant and c is the velocity of light in a vacuum. The wavelength $\lambda_v$ can excite only molecules occupying vibronic level 72 and, to a smaller extent, molecules occupying slightly higher levels, the excitation of which is represented by the dotted vertical line 91. Luminescence emission of wavelengths $\lambda_f$ occurs from sublevel 80 to the vibronic levels of the ground electronic level, said emission represented by lines 92, 93, 94 and 95. As shown in FIG. 8, a considerable spectral portion of the emission occurs at photon energies higher (and wavelengths shorter) than that of the excitation light, and is commonly referred to as anti-stokes emission.

In practice the vibronic material is often used as a solid solution, glassy or crystalline, which constitutes the temperature probe. The concentration of the vibronic material and the dimension of the probe along the direction of the interrogating light are chosen so that the probe absorbs only a fraction $\alpha$ of the intensity of the nearly monochromatic excitation light within the temperature range of operation, and transmits the rest. The absorbed fraction obeys the relation $$\alpha = 1 - 10^{-\epsilon c\, d(N/N)} \tag{3}$$

where $\epsilon$ is the molar decadic absorption coefficient of the molecules occupying the vibronic level 72;

$c_o$ is the molar concentration of the vibronic material;

d is the probe length in the direction of the incident excitation light;

$N_{72}$ is the number of molecules of the vibronic material occupying vibronic level 72; and N is the total number of molecules of the vibronic material.

The ratio $N_{72}/N$ essentially follows the relation $$N_{72}/N = f^{-1} \exp(-E_v/kT) \tag{4}$$

where f is the so-called partition coefficient of the molecular system, k is the Boltzmann constant and T is the absolute temperature. The expression $c_o \cdot f^{-1} \exp(-E_v/kT)$ is essentially the effective molar concentration of the molecules of the vibronic material occupying the vibronic level 72, and the quantity $10_{-\epsilon c\, d(N/N)}$ is the fraction of the intensity of the interrogating light transmitted by the probe (assuming no other light losses) and equal to $(1-\alpha)$. The ratio $E_v/k$ can be designated by the single constant $\beta$, for a given wavelength $\lambda_v$.

At optical densities no greater than about 0.02 $\alpha$ is given approximately by $$\alpha \approx 2.3 \epsilon c_o d f^{-1} \exp(-E_v/kT) \tag{5}$$

An analogous expression to $f^{-1}\exp(-E_v/kT)$ is $[\exp(E_v/kT) - 1]^{-1}$, generally known as the Bose-Einstein population factor. As the value of $(E_v/kT)$ increases, especially at values greater than 3.0, the Bose-Einstein population factor becomes closer in magnitude to the Boltzmann factor $\exp(-E_v/kT)$.

At optical densities greater than 0.02 the relationship between α and the Boltzmann factor exp(-$E_v$/kT) becomes less linear, but equations (3) and (4) still hold, and the method can be used at high, low or intermediate optical densities.

The luminescence intensity $I_f$ generated by the interrogating light absorbed by the probe obeys the relation $$I_f = P_o(\lambda_v/hc)\alpha\phi \text{ photons.sec}^{-1} \quad (6)$$

where $P_o$ is the radiant power, in watts, of the incident interrogating light, and φ is the luminescence quantum efficiency of the vibronic material.

Probes made from materials having high φ values can produce large signal-to-noise ratios even with optical densities lower than 0.01, provided that the optical system has at least a moderately high collection efficiency for the probe luminescence. Such efficiency is easily obtainable with state-of-the-art systems.

The sum of the light intensity absorbed and the light intensity transmitted by a clear medium is constant. Therefore, as the magnitude of the absorbed fraction α increases with increasing temperature according to equation (5), the intensity of the transmitted light must decrease accordingly. Since according to equation (6) the luminescence light intensity is proportional to α, it follows that the ratio of the intensity of the luminescence light to that of the transmitted light increases with increasing temperature, and this ratio can be used as a temperature indicator. The ratio is unaffected or minimally affected by fluctuations of the intensity of the interrogating light or by fiber and/or connector losses.

The temperature coefficient of the luminescence intensity follows approximately the relation $$(1/I_o)(dI_f/dT) = E_v/kT^2 = \beta/T^2 \quad (7)$$

where $I_o$ is the luminescence intensity at a chosen reference temperature. For example, a material with an energy $E_v$ of 1200 cm$^{-1}$ has a coefficient of about two percent per kelvin at an ambient temperature of 295K.

Equations (5) to (6) show that the method of the preceding paragraphs requires only a temperature-dependent change in the optical absorption coefficient of the photoluminescent probe material at wavelengths corresponding to photon energies lower than the energy $E_s$ of the excited emissive level. This property is shared by virtually all solid and liquid photoluminescent materials. The method does not require any temperature-dependent changes in the luminescence quantum efficiency, spectral distribution or decay time. Therefore, and in contrast to all other prior art methods, it can be implemented with most efficient photoluminescent materials.

Figure 9:
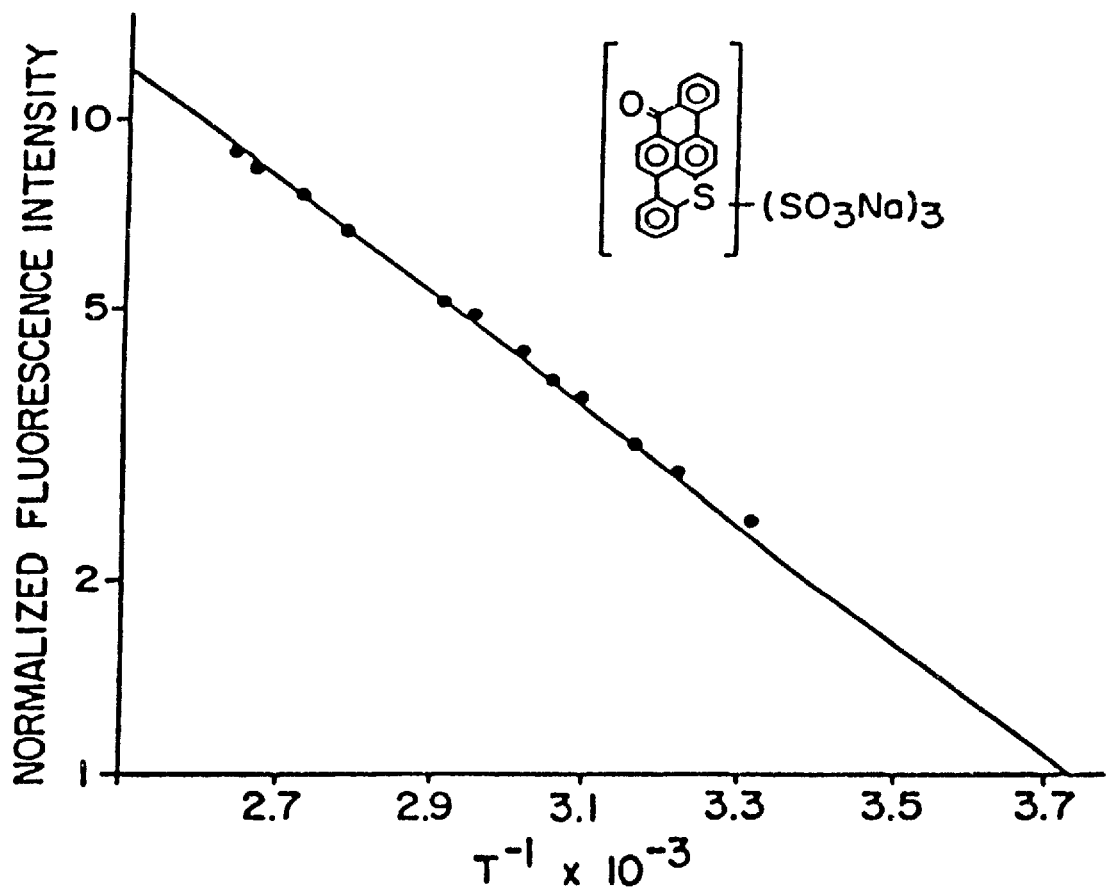
FIG. 9 shows the temperature dependence of the fluorescence intensity of a fluorescent material operated according to the principles illustrated in FIG. 1.

Experimental tests of equations (5) to (7) have been carried out, and the behavior predicted by the equations was verified. FIG. 9 shows actual normalized fluorescence intensity as a function of the inverse absolute temperature of a dimethyl sulfoxide (DMSO) solution of the dye represented by the formula

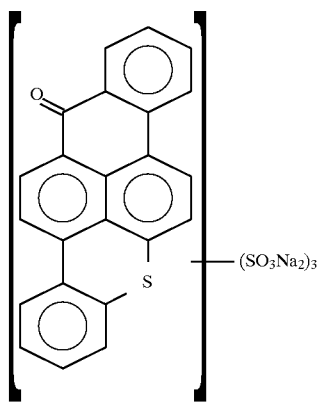

illuminated by a light beam from a helium-neon laser. The dye concentration was approximately 10$^{-4}$ Molar, with a path length of 1 cm. The fluorescence intensity was monitored at wavelengths of 610±2 nanometers (nm), shorter than the laser beam wavelength of 632.8 nm. The superiority of this method of temperature measurement compared to that based on light transmission measurements becomes evident from the fact that over the temperature interval from about 300K (27° C.) to about 400K (127° C.) the light transmission of the dye solution varies by less than two percent, while the intensity ratio of fluorescence light to transmitted light varies by about an order of magnitude.

In the simplest embodiment of the method for temperature measurement according to this section, one only has to interrogate the luminescent probe material with light of a wavelength or wavelengths at which the probe material has a temperature-dependent absorption coefficient, and measure the intensity of the luminescence generated by the absorbed interrogating light. While the probe in the example of FIG. 9 is a liquid solution, solid probes, preferably in the form of optical fibers or inorganic crystalline materials, can also be used and are preferred in practical devices. As known to those of ordinary skill in the art, most inorganic photoluminescent materials wherein the luminescence centers are definite, stabe atomic or molecular entities like transition metal ions and rare earth ions in a stable oxidation state, have luminescence properties which are unique and repeatable for each temperature within a temperature range typical for a specific material.

The above method can be implemented with any photoluminescent probe material having at least one energy level which can be thermally populated from the ground level to an extent that varies as a function of temperature. Such thermally populated level does not have to be a vibrational level or sublevel. It can be, for example, an electronic sublevel of the ground electronic level of a rare earth ion like Nd$^{3+}$. In this case, if the probe is interrogated with light of wavelengths of about 950 nm or other suitable wavelengths, the absorbed fraction α$P_o$ of the interrogating light intensity, and hence the Nd$^{3+}$ luminescence intensity, increase with increasing temperature.

If the probe material is a glass or an optically homogeneous plastic, it can be made into an optical fiber.

An optical fiber temperature probe based on the measurement of a temperature-dependent light absorption measurement has an advantage over other optical probes in that it measures the average temperature over the length of the fiber probe. Thus, if one wishes to measure the average temperature over, for example, a pipe having different temperatures along its length, a long fiber temperature probe disposed over the whole length of the pipe will measure its average temperature. A preferred embodiment uses a photoluminescent probe with a temperature-dependent light absorption, the luminescence intensity of which follows approximately equation (6). Glass fibers doped with $Nd^{3+}$, $UO_2^{2+}$, $Mn^{2+}$ or any other photoluminescent ion are suitable. Also suitable, especially at temperatures not much higher than about 150° C., are plastic fibers doped with any plastic-soluble, stable fluorescent dye.

3.1 Fiber optic temperature sensors covering the temperature range from the lower cryogenic regions up to over 800° C., using a single probe.

FIG. 8 and equations (5) and (7) suggest how one may use a single probe for measuring temperatures over a very wide range from the lower cryogenic regions up to over 800° C., using a single probe with a high luminescence efficiency at these high temperatures, for example $Nd^{3+}$-doped yttrium aluminum garnet (Nd:YAG). One may choose the value of $E_v$ for each part of the range simply by choosing the wavelength $\lambda_v$ of the excitation source. Equation (7) suggests the $E_v$ values one may choose for any temperature range. Suppose than one requires a temperature coefficient of the signal of 0.01 or greater. At ordinary temperatures one may then use excitation wavelengths of about 950 nm from an inexpensive LED, corresponding to an $E_v$ value of about 750 $cm^{-1}$ and a signal temperature coefficient of about 0.012. For measuring cryogenic temperatures one can use a temperature-tunable diode laser emitting from about 807 nm to about 820 nm, spanning a range of selectable $E_v$ values from about 10 to about 200 $cm^{-1}$, usable from about 4.2K to about 60K. For temperatures higher than 600K one may use a Nd-doped laser at 1.06 $\mu$m, corresponding to an $E_v$ value of about 1950 $cm^{-1}$. The high luminescence efficiency of Nd:YAG at the above high temperatures was reported by Grattan et al., *IEE Proceedings, Vol.* 134, pp 291–294 (1987). Grattan et al. used the probe in the prior art conventional method based on the measurement of the temperature-dependent luminescence decay time $\tau$. The method has a very low sensitivity as the relative change in $\tau$ per kelvin is only of the order of 0.0001 $\tau$, in contrast to relative changes two orders of magnitude greater obtainable with the techniques of this invention as discussed in section 3.0. Used according to the teachings of this invention, temperature probes based on Nd:YAG and other probes having a high luminescence efficiency at high temperatures have the additional and obvious advantage that, at the higher temperature range of their operation in the luminescence mode they emit the strongly temperature- dependent black body radiation of wavelengths within the range of operation of the same ordinary silicon photodetectors used for measuring the photoluminescence of the probe. If one uses, for example, the same Nd:YAG probe mentioned above at the end of a heat-resistant fiber made of sapphire, the intensity of the black body radiation at the wavelength of, say, 1.0 $\mu$m, will be an accurate temperature indicator from about 800K to about 1,900° C. One can thus measure temperature anywhere from near absolute zero to well over 1500° C. with a single probe and a single photodetector. The above referenced paper by Grattan et al. actually discusses the black body radiation emitted by Nd:YAG at temperatures of 800K (527° C.) and higher, overlapping the photoluminescence from the same material.

3.2 An infrared Image Converter Based on Thermally Activated Light Absorption.

The teachings of this invention can be applied to the construction of a sensitive infrared-to-visible image converter. It was shown in section 3.0 that the absorption of light of photon energy lower than the energy of a luminescent level of a material is strongly temperature-dependent. This fact can be used as a basis for constructing sensitive infrared-to-visible image converters, especially at liquid helium temperatures. A probe which absorbs infrared radiation undergoes a temperature increase $\Delta T$. Referring to FIG. 8 and equation (7) of section 3.0, it can be noticed that for any value of ($E_v/kT$) the temperature coefficient of the luminescence intensity $I_f$ increases as the initial absolute temperature decreases. The relative increase $\Delta I_f$ in the luminescence intensity follows the relation $$\Delta I_f/I_o = (E_v/kT^2)\Delta T \qquad (8)$$

or $$\Delta I_f/I_o = (E_v/kT^2)(H/C_v) \qquad (9)$$

where H is the heat generated by the absorbed infrared radiation and $C_v$ is the specific heat of the probe. It is known that the specific heat of essentially all materials is orders of magnitude smaller at liquid helium temperatures than at ordinary temperatures. Thus, if the probe is made thin to reduce its thermal mass, a relatively low intensity of infrared radiation can be converted into a substantial increase of the intensity of the fluorescence light emitted by the probe.

Now consider a photoluminescent probe in the form of a thin two-dimensional film of low thermal mass, on which a thermal infrared image is focused. Each image element of the infrared image will create a photoluminescent image element of a size determined by the infrared wavelength and the optical characteristics of the focusing system. Each photoluminescent image element also represents a discrete temperature sensor wherein a temperature change generated by the incident infrared radiation causes a change in the magnitude of the fraction $\alpha$ of the intensity of the interrogating light of wavelengths $\lambda_v$ which is absorbed by the element, thus generating luminescence light of intensities which vary according to equations (7), (8) and (9). Therefore, the thermal infrared image focused on the film will be converted into a photoluminescence image having a two-dimensional luminescence intensity distribution correlated with the two-dimensional intensity distribution of the infrared image.

A preferred embodiment of an infrared image converter according to this invention uses a film similar to that illustrated in FIG. 7, except that the layer 56 has dissolved therein a photoluminescent material as described in section 3.0 and FIG. 8, the interrogating light has wavelengths $\lambda_v$ as defined in said section 1.0, and both layers 58 and 60 have indices of refraction substantially lower than the index $n_1$ of layer 56, and could be comprised of inorganic glass as well as organic plastic material. As shown in section 3.0 and FIG. 8, the luminescence light emitted by the photoluminescent material may include wavelengths shorter from the wavelengths $\lambda_v$ of the interrogating light.

Although the invention described in this section and the one described in section 2.1 both use a film for converting a thermal infrared image into an image having wavelengths shorter than those of the thermal infrared radiation, the two inventions are fundamentally different in that the underlying physical processes are very different, and neither of them anticipates the other. In the invention described in section 2.1 the physical process is the deflection of interrogating light injected into the film from one layer of the film to another layer, the deflection being caused by temperature-dependent changes in the relative values of the indices of refraction of these two layers caused by the heating effect of the incident infrared radiation. This deflection of light does not involve any light absorption. To the extent that the deflected light in converted into luminescence light in the alternate embodiment using a fluorescent dye, this conversion occurs after the thermal effect of the infrared image on the film, that is, after the light deflection, and does not involve any temperature-dependent change of the magnitude of the absorbed fraction $\alpha$ of the intensity of the interrogating light of wavelengths $\lambda_v$. In the invention described in this section, by contrast, the thermal effect of the infrared image on the film is the increase of the absorption coefficient, and hence of the magnitude of said fraction $\alpha$, of the intensity of the interrogating light of wavelengths $\lambda_v$ which is absorbed by the photoluminescent material dissolved in a layer of the film, independent or only minimally dependent on any changes in the index of refraction of said layer. There is no appreciable deflection of the intensity of the interrogating light from one layer of the film to another.

Since certain changes may be made in the foregoing specification without departing from the scope of the invention herein disclosed, it is intended that all matter contained in the above description and/or depicted in the accompanying drawings be construed in an illustrative and not in a limiting sense.

I claim:

1. An arrangement for sensing a temperature rise at a multiplicity of sensing points simultaneously on a two-dimensional film light guide, comprising:
    (a) a two-dimensional film light guide including a first layer comprised of a clear material having an index of refraction $n_1$ in contact with a second layer comprised of a material with an index of refraction $n_2$ lower than $n_1$, wherein the temperature coefficient of $n_1$ is substantially greater than the temperature coefficient of $n_2$ and decreases with an increase of temperature;
    (b) light source means for injecting light of visible or near infrared wavelengths $\lambda_1$ into at least one edge of said first layer of said light guide, a fraction of the intensity of said light being deflected into said second layer under said temperature rise at each of said sensing points, the intensity of said deflected light being a function of the magnitude of the temperature rise at said point; and
    (c) photodetection means for sensing the intensity of said light of wavelengths $\lambda_1$ which is deflected into said second layer simultaneously from each and all said sensing points, said intensity being an indicator of the magnitude of the temperature rise at that point.

2. An arrangement as claimed in claim 1 and adapted to sense infrared radiation incident on said film light guide, wherein said film light guide is provided with an infrared-absorbing material and said temperature rise at each of said sensing points is caused by the absorption of said infrared radiation by said infrared-absorbing material, the magnitude of the temperature rise at that sensing point being an indicator of the intensity of the infrared radiation incident on that point.

3. An arrangement as claimed in claim 2 wherein said second layer has applied thereto a third layer having dissolved therein a photoluminescent material characterized by absorbing at least a fraction of the intensity of said light of wavelengths $\lambda_1$ which is deflected into said second layer at each sensing point and by emitting photoluminescence radiation of wavelengths $\lambda_2$ the intensity of which is an indicator of the temperature rise and, hence, of the intensity of the infrared radiation absorbed by said infrared-absorbing material at each sensing point.

4. An arrangement as claimed in claim 3 and adapted to convert an infrared image into a visible or near infrared image of wavelengths $\lambda_2$, wherein said photodetection means is a photoelectronic imaging device, the arrangement additionally comprising:
    (a) optical means for focusing the infrared image into said film light guide, thereby generating a luminescence light image of wavelengths $\lambda_2$ having a two-dimensional intensity distribution indicative of the two-dimensional intensity distribution of the thermal infrared image focused on said film light guide; and
    (b) optical means for focusing said luminescence light image of wavelengths $\lambda_2$ on said photoelectronic imaging device.

5. An arrangement as claimed in claim 2 wherein said film light guide additionally includes a light-scattering layer for scattering out of the plane of said film light guide said light of wavelengths $\lambda_1$ deflected out of said light-scattering layer.

6. An arrangement as claimed in claim 5 and adapted to convert an infrared image into a visible or near infrared image of wavelengths $\lambda_1$, wherein said photodetection means is a photoelectronic imaging device, the arrangement additionally comprising:
    (a) optical means for focusing the infrared image into said film light guide, thereby generating a visible light image of wavelengths $\lambda_1$ having a two-dimensional intensity distribution indicative of the two-dimensional intensity distribution of the thermal infrared image focused on said film light guide; and
    (b) optical means for focusing said luminescence light image of wavelengths $\lambda_1$ on said photoelectronic imaging device.

7. A method for sensing a temperature rise at a multiplicity of sensing points simultaneously on a two-dimensional film light guide, comprising the steps of:
    (a) providing said two-dimensional film light guide including a first layer comprised of a clear material having an index of refraction $n_1$ in contact with a second layer comprised of a material with an index of refraction $n_2$ lower than $n_1$, wherein the temperature coefficient of $n_1$ is substantially greater than the temperature coefficient of $n_2$ and decreases with an increase of temperature;
    (b) injecting light of visible or near infrared wavelengths $\lambda_1$ into at least one edge of said first layer of said light guide, a fraction of the intensity of said light being deflected into said second layer under said temperature rise at each of said sensing points, the intensity of said deflected light being a function of the magnitude of the temperature rise at that point; and
    (c) sensing, with photodetection means, the intensity of said light of wavelengths $\lambda_1$ which is deflected into said second layer simultaneously from each and all said sensing points, said intensity being an indicator of the magnitude of the temperature rise at that point.

8. A method as claimed in claim 7 and adapted to sense infrared radiation incident on said film light guide, wherein said film light guide is provided with an infrared-absorbing material and said temperature rise at each of said sensing points is caused by the absorption of said infrared radiation by said infrared-absorbing material, the magnitude of the temperature rise at that sensing point being an indicator of the intensity of the infrared radiation incident on that point.

9. A method as claimed in claim 8 wherein said second layer has applied thereto a third layer having dissolved therein a photoluminescent material characterized by absorbing at least a fraction of the intensity of said light of wavelengths $\lambda_1$ which is deflected into said second layer and by emitting photoluminescence radiation of wavelengths $\lambda_1$ the intensity of which is an indicator of the temperature rise and, hence, of the intensity of the infrared radiation absorbed by said infrared-absorbing material.

10. A method as claimed in claim 9 and adapted to convert an infrared image into a visible or near infrared image of wavelengths $\lambda_2$, additionally comprising the steps of:

(a) focusing the infrared image into said film light guide, thereby generating a luminescence light image of wavelengths $\lambda_2$ having a two-dimensional intensity distribution indicative of the two-dimensional intensity distribution of the thermal infrared image focused on said film light guide; and (b) focusing said luminescence light image into photo-electronic imaging means for processing said luminescence light image into a visible display.

11. A method as claimed in claim 8 wherein said film light guide additionally includes a light-scattering layer for scattering out of the plane of said film light guide said light of wavelengths $\lambda_1$ deflected out of said light-scattering layer.

12. A method as claimed in claim 11 and adapted to convert an infrared image into a visible or near infrared image of wavelengths $\lambda_1$, additionally comprising the steps of:

(a) focusing the infrared image into said film light guide, thereby generating a light image of wavelengths $\lambda_1$ having a two-dimensional intensity distribution indicative of the two-dimensional intensity distribution of the infrared image focused on said film light guide; and (b) focusing said light image of wavelengths $\lambda_1$ into photo-electronic imaging means for processing said luminescence light image into a visible display.

* * * * *